United States Patent [19]
DeWitt et al.

[11] Patent Number: 5,803,987
[45] Date of Patent: Sep. 8, 1998

[54] MULTI-TIP WASH STATION FOR ROBOT

[75] Inventors: Sheila DeWitt, Clinton; Alice Mensch, Ann Arbor; Russell Rhoton, Manchester, all of Mich.

[73] Assignee: Warner-Lambert Company, Morris Plains, N.J.

[21] Appl. No.: 785,264

[22] Filed: Jan. 17, 1997

[51] Int. Cl.⁶ .................................................. B08B 3/04
[52] U.S. Cl. ........................................ 134/25.4; 134/170
[58] Field of Search ............................ 134/22.18, 25.4, 134/166 R, 169 R, 170; 73/864.22, 864.23, 864.24; 422/104; 436/49, 180

[56] References Cited

U.S. PATENT DOCUMENTS

| | | |
|---|---|---|
| 3,960,020 | 6/1976 | Gordon et al. . |
| 4,730,631 | 3/1988 | Schwartz . |
| 4,748,007 | 5/1988 | Gaudion et al. ................ 134/170 X |
| 4,948,563 | 8/1990 | Kanewske, III . |
| 5,066,336 | 11/1991 | Hoffman et al. . |
| 5,186,194 | 2/1993 | Kitajima ........................ 134/170 X |
| 5,229,074 | 7/1993 | Heath et al. . |
| 5,578,270 | 11/1996 | Reichler et al. ................. 436/49 X |
| 5,660,792 | 8/1997 | Koike ........................... 73/864.24 X |

OTHER PUBLICATIONS

Monique Freund, et al, "Experimental Thrombosis on a Collagen Coated Arterioarterial Shunt in Rats: A Pharmacological Model to Study Antithrombotic Agents Inhibiting Thrombin Formation and Platelet Deposition," *Thrombosis and Haemostasis*, vol. 69, No. 5, 1993, pp. 515–521.

Steven R. Hanson, et al "Platelet Interactions with Dacron Vascular Grafts–A Model of Acute Thrombosis in Baboons," Arteriosclerosis, vol. 5, No. 6, Nov./Dec. 1985, pp. 595–603.

Stan Hollenbach, et al "A Comparative Study of Prothrombinase and Thrombin Inhibitors ia a Novel Rabbit Model of Non–Occlusive Deep Vein Thrombosis," *Thrombosis and Haemostasis*, vol. 71, No. 3, 1994, pp. 357–362.

Gilberto L. Nunes, et al, "Inhibition of Platelet–Dependent Thrombosis by Local Delivery of Heparin With a Hydrogel–Coated Balloon," *Circulation*, vol. 92, No. 7, Oct. 1, 1995, pp. 1697–1700.

*Primary Examiner*—Philip R. Coe
*Attorney, Agent, or Firm*—Charles W. Almer

[57] ABSTRACT

A wash station for washing probes which are used with robotic systems. In particular, the wash station is used with robotic systems to provide simultaneous cleaning of both the interior and the exterior of multiple probes employed by the system. The wash station consists of a base, multiple chambers and multiple cylinders. The robotic probe to be cleaned is inserted within one of the cylinders where it is immersed in wash liquid to wash the exterior walls. The cylinders are separated by chambers. The wash liquid is removed from the wash station via a drain located in the base. In a preferred embodiment, independent access for each probe into the wash station is provided. In addition, the wash station provides a large capacity for fluid handling and is constructed such that the station is water tight. In a particularly preferred embodiment, the wash station is constructed from chemically compatible materials which will not be affected by exposure to the materials needed for general chemical synthesis.

15 Claims, 6 Drawing Sheets

MULTI-TIP WASH STATION FOR ROBOT

BACKGROUND OF THE INVENTION

1. Field of the Invention

This invention relates to an apparatus for use with robotic systems and, in particular to a wash station having multiple sites for washing of multi-tip probes at robot stations.

2. Description of Related Art

Robotics and robotic systems are utilized for many different functions. One example of an important function carried out by robotic systems is chemical synthesis, such as that described in co-pending United States patent application Ser. No. 08/475,559, which is incorporated herein by reference. During processes such as chemical synthesis, multiple probes are often employed in conjunction with various diverse materials. For example, the handling of liquid samples and the transferring of reagent and/or resin slurries is often carried out with a robotic sample processor. The use of the sample processor increases the speed and precision of the sample handling and also allows the reproducibility and transfer of samples to discreet locations without operator error. In order to achieve the full benefits of the robotic system, it is advantageous to utilize a process having multiple dispensing and aspirating probes. At different stages of the process, it is critical that the probes and, more particularly, the probe tips, be thoroughly cleaned.

Currently available devices for cleaning robotic system probes have a number of drawbacks and disadvantages. First, there are no robotic cleaning stations which are capable of simultaneously accommodating more than one probe tip. This is a significant disadvantage in that a substantial amount of additional time and effort is necessary in order to clean the multiple probes which are employed in most systems. Further, currently available cleaning stations do not entirely immerse the full length of the probe and are incapable of cleaning the entire probe, both inside and outside. This feature is critical when the probe is completely immersed in reagents for aspiration of solutions. Most robotic systems overcome the need to immerse more than the probe tip (which is usually about ½ inch long) in a solution by utilizing infrared or conductive level detection. However, solvents, utilized in organic chemistry, are not detected well by this method. Therefore, efficient aspiration is only achieved by withdrawing solutions from the bottom of the container. This is a further significant disadvantage in that contaminants, such as organic solvents, may remain on the outside of the probe following cleaning on the currently used stations.

Consequently, it is an objective of the present invention to provide a wash station for robotic systems which will provide simultaneous cleaning of multiple probe tips employed by the system. It is a further objective of the present invention to provide a wash station which will thoroughly clean both the inside and the outside of the probe tips.

SUMMARY OF THE INVENTION

The present invention is directed to a wash station for use with robotic systems. In particular, the present invention is directed to a wash station for use with robotic systems which will provide simultaneous cleaning of both the interior and the exterior of multiple probes employed by the system. In the preferred embodiment, independent access for each probe into the wash station is provided. In addition, the wash station provides a large capacity for fluid handling and is constructed such that the station is water tight. In a particularly preferred embodiment, the wash station is constructed from chemically compatible materials which will not be affected by exposure to the materials needed for general chemical synthesis.

DESCRIPTION OF THE PREFERRED EMBODIMENTS

Reference will now be made in detail to the presently preferred embodiments of the invention.

The apparatus of the present invention comprises a multi-tip wash station for use with robotic systems. The wash station (10) illustrated in FIGS. 1–5 comprises sites for four separate, simultaneous probe washes, however fewer or more sites could be provided, as desired, and would be within the scope of the invention. A first element of the apparatus is the cylinders (11). Each cylinder (11) is of sufficient length and diameter to receive a system probe in its entirety. Hole (15) is located on the top end of each cylinder (11) and is of sufficient diameter and length to accommodate a probe. The cylinder is substantially hollow and open throughout its entire length. Alternatively, the cylinder may be closed at one end. In order to utilize the present invention, a probe from a robotic system is inserted into hole (15) for cleaning. Each hole is capable of accommodating only one probe, consequently independent access and containment of each probe is ensured. In order to accommodate the various materials which may have been utilized in the robotic system and the materials necessary to wash the probes, it is advantageous if the cylinder is constructed from a chemically corrosion-resistant material. Examples of such useful materials are teflon and delrin.

Figure 1:
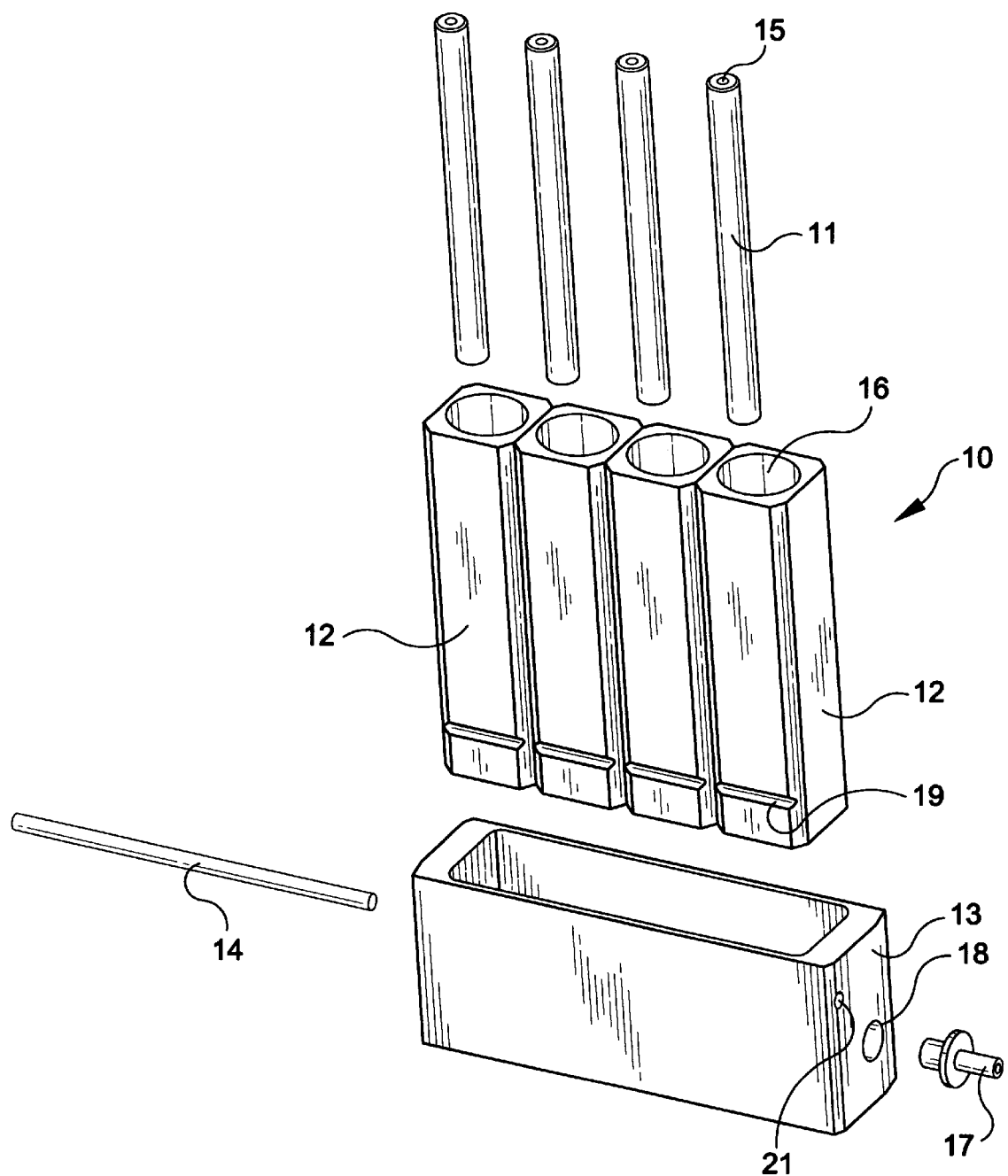
FIG. 1 is an exploded, perspective of the wash station of the invention.
Figure 2:
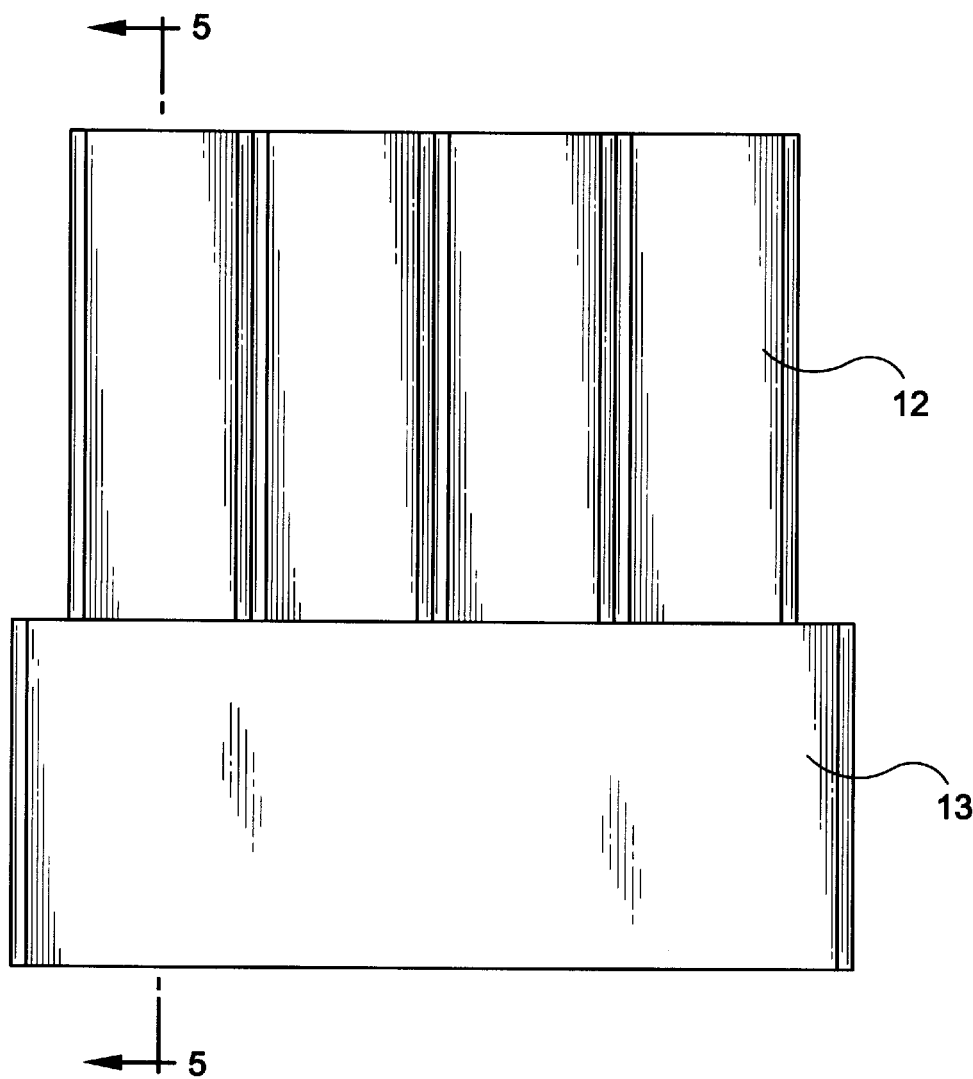
FIG. 2 is a side view of the wash station of the invention.
Figure 3:
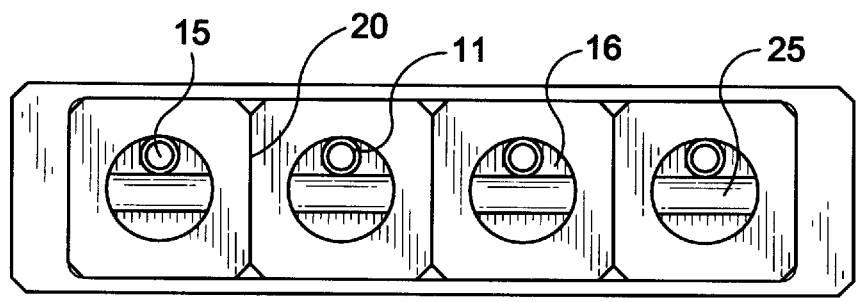
FIG. 3 is a top view of the wash station of the invention.

A further element of the invention is the chamber (12) which is adapted to hold one cylinder (11). Each chamber (12) is substantially hollow and contains an opening (16) which extends throughout the entire length of the chamber. Four such chambers are illustrated in FIGS. 1–4, however any desired number of chambers may be utilized so as to conform with the number of probes being utilized. As best illustrated in FIG. 3, walls (20) separate each of the chambers and prevent contamination between probes in separate chambers. The chambers (12) are preferably constructed from a material which will be resistant to the materials required for dispensing excess reagents and washing probes and for carrying out various reactions.

Figure 5:
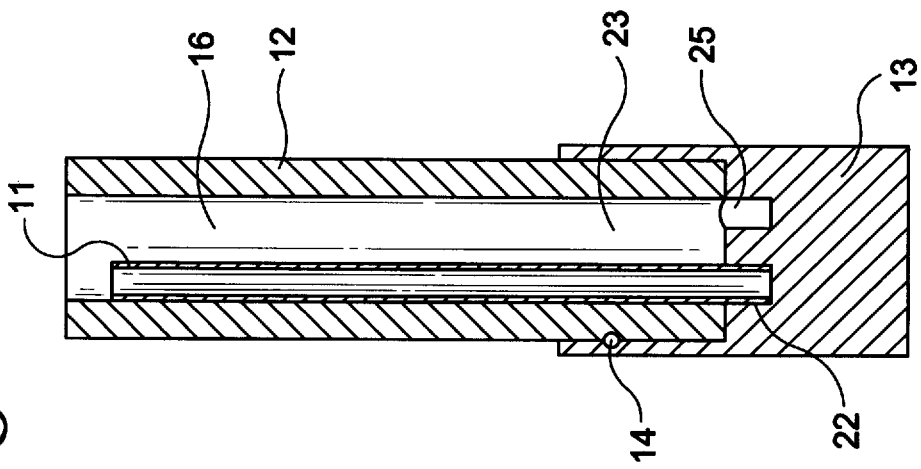
FIG. 5 is a cross-section along line 5—5 of the wash station of the invention.
Figure 4:
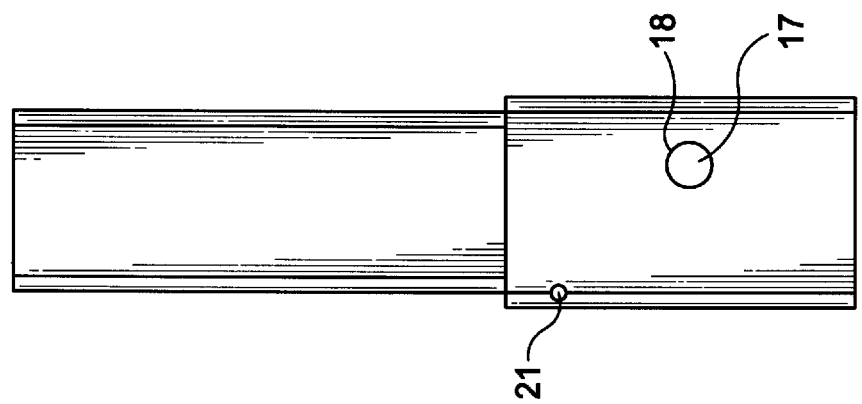
FIG. 4 is an end view of the wash station of the invention.

Base (13) is provided to accommodate the lower ends of chambers (12). As illustrated in FIG. 5, one embodiment of the wash station provides for a tight friction fit between the lower end of the chambers and the base such that the chambers will fit snugly within the base. Base (13) contains a plurality of pockets (22) which are sufficient in size to receive the lower ends of the cylinders and a drain channel (25) which may be located adjacent to the pockets and extends throughout the entire length of the base and allows the waste liquid to flow away from the chambers. As illustrated in FIG. 5, means for removing the waste liquid are included in the base. Preferably, the means are in the form of an opening (18) which is located on the base, preferably at one end, and aligned with drain channel (25) such that the waste liquid may be removed from the base via this opening. Plug (17) is provided such that the removal of the waste is controlled and adapted readily to available tubing. In a preferred embodiment, alignment means are provided to align the chambers within the base. A preferred alignment means is a dowel (14) which extends through openings (21) in the base and groove (19) in the chambers. As illustrated in FIGS. 3 and 5, the cylinder (11) is preferably inserted into chamber (15) along one of the side walls of the chamber.

Figure 6:
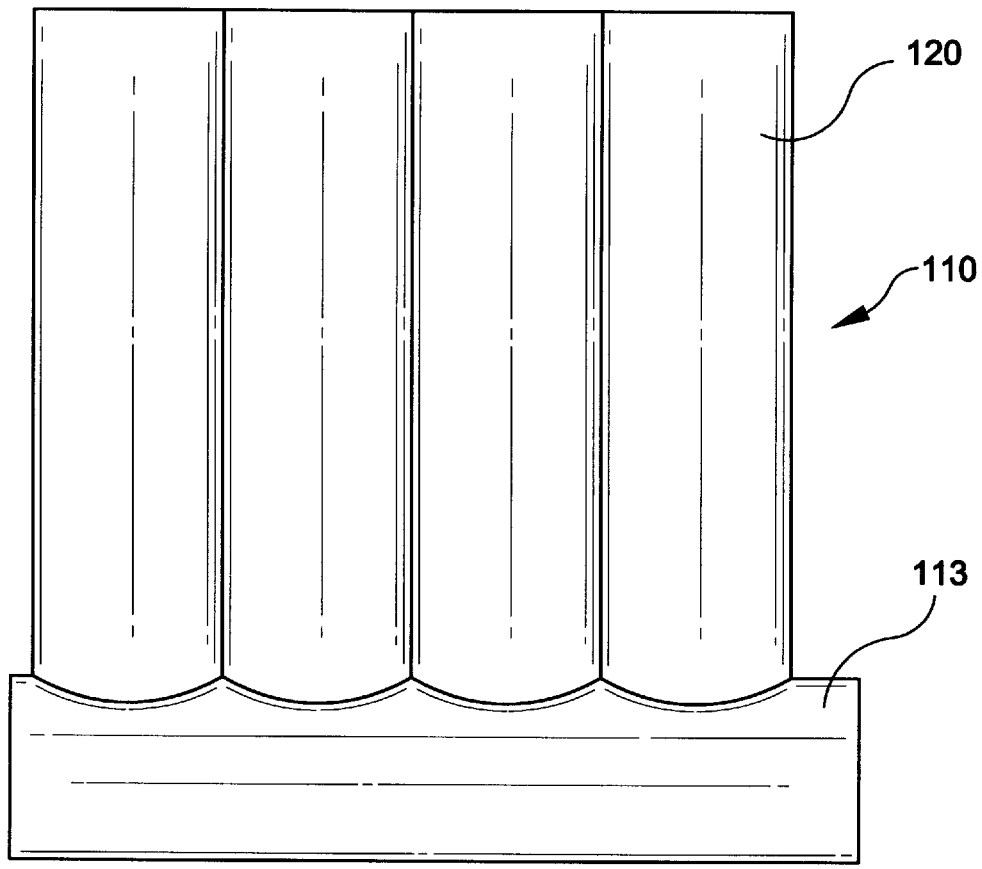
FIG. 6 is a side view of a further embodiment of the wash station of the invention.
Figure 7:
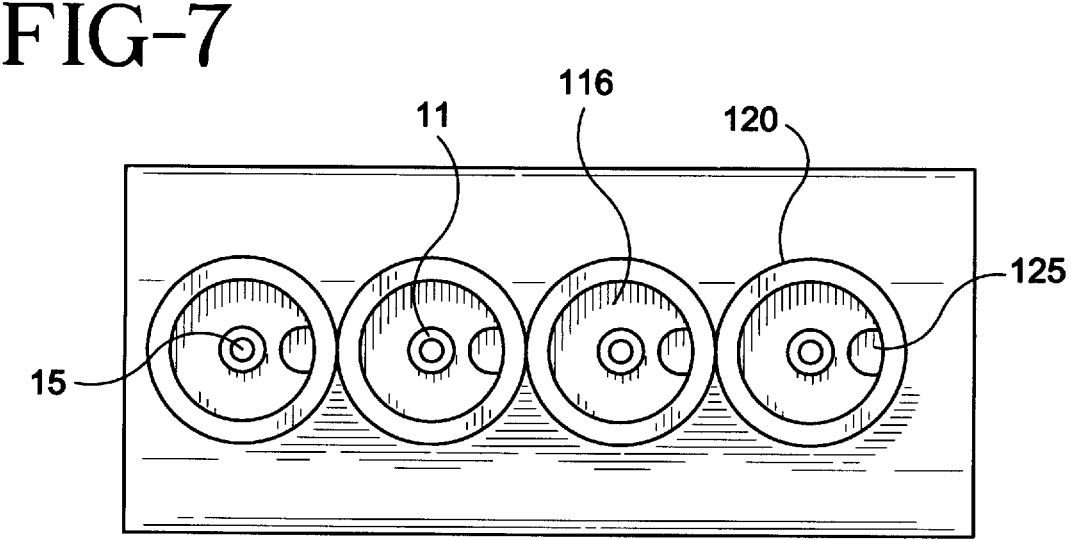
FIG. 7 is a top view of a further embodiment of the wash station of the invention.
Figure 8:
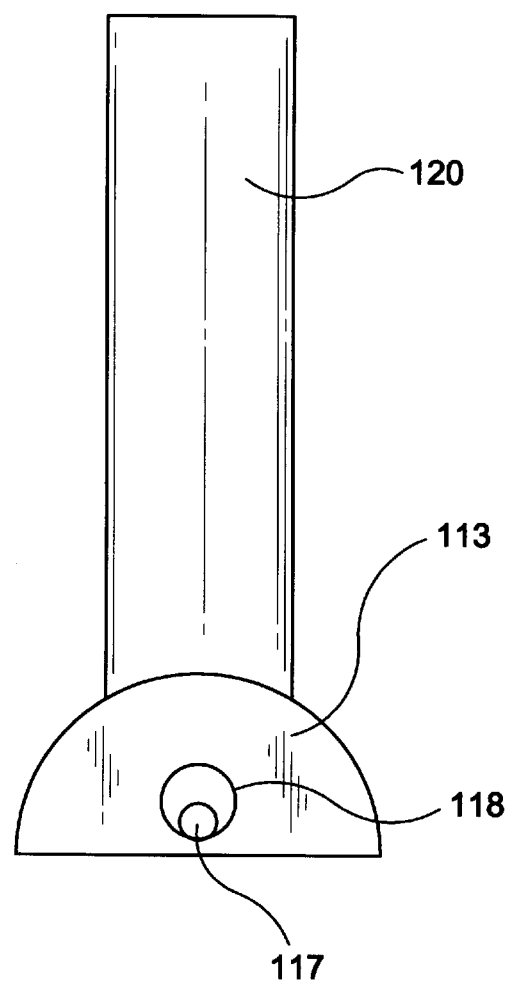
FIG. 8 is an end view of a further embodiment of the wash station of the invention.

While the chambers illustrated in FIGS. 1–5 are substantially square and the base of those figures is substantially rectangular, depending upon the robotic system with which the wash station is being utilized, different shaped wash stations may be desired and the wash station of the invention may be of any desired shape. FIGS. 6–8 illustrate a wash station (110) having circular chambers (120) and a semicircular base (113). Cylinders (11) are utilized within chambers (120) having openings (116). Drain channels (125) allow for drainage of waste material which flows out of opening (118) and through the plug (117).

Figure 9:
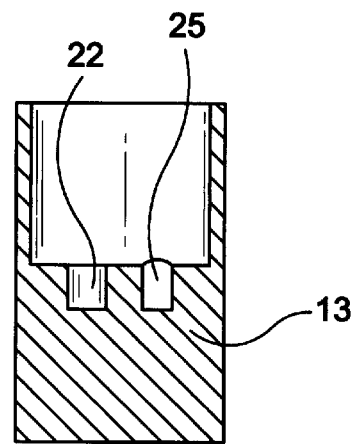
FIG. 9 is a cross-section view of the base of the wash station of the invention.

FIG. 9 illustrates a cross-section of a preferred embodiment of the base. Pocket (22) is provided to accommodate the lower end of the cylinder (11). During use, the lower end of the cylinder fits tightly into the pocket such that liquid cannot escape from the lower end of the cylinder. Consequently, wash liquid is forced upward around the outside walls of the probe which is within the cylinder. The tight fit between the cylinder and the pockets allow the entire probe, both inside and outside, to be washed. Drain channel (25), located adjacent to the pocket, provides a route for the waste liquid to flow away from the cylinders and probes.

Figure 10:
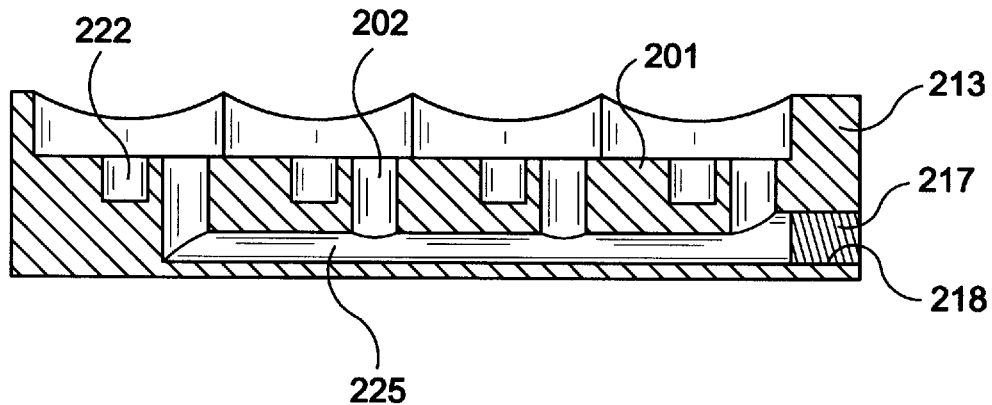
FIG. 10 is a cross-section view of the base of a further embodiment of the wash station of the invention.

FIG. 10 illustrates a preferred embodiment of the base unit of the wash station. In this preferred embodiment, base unit (213) contains pockets (222) for receiving the lower ends of cylinders. Abutments (201) are provided for accommodating the lower ends of the chambers. Individual drains (202) are provided for individually draining the waste liquid from each separate chamber. The individual drains (202) all flow into central drainage channel (225) which is aligned with opening (218) for drainage of the waste liquid out of the unit. Plug (217) may be utilized to interface with the drain and for control of the flow of waste liquid from the unit. During usage of the base of this preferred embodiment, the cylinders fit into the pockets, the walls of the chambers rest on the abutments and the hollow opening of the chamber is aligned with the individual drains to facilitate drainage from the chambers.

Figure 11:
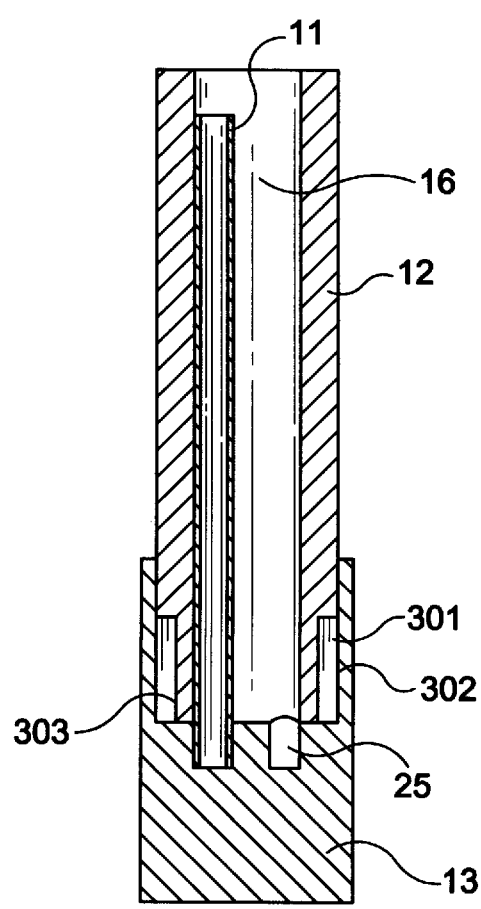
FIG. 11 is a cross-section view along line of the wash station of the invention.

FIG. 11 illustrates a preferred embodiment of the chamber. In this preferred embodiment, the walls on the lower end of the chamber are less thick than the walls on the top end of the chamber. Opening (301) is created between the inside wall (302) of the base and the reduced wall portion (303) of the outside wall of the chamber. A preferred dimension of the opening is approximately 1/16 of an inch. As a result of the reduced wall portion of the chamber, the chamber is only partially pressure fitted within the base. The partial press fit allows for the easier removal of the chamber from the base. Further, the opening (301) eliminates the problem of capillary action of the waste wash liquid on the walls between the base and the chamber.

In any of the embodiments set forth the base, chambers, and cylinders may be constructed as one integral unit, as separate modular components, or as any combination of an integral unit with modular components. In the preferred embodiment, the base, chambers and cylinders are each separate modular units which are adapted such that the cylinders fit within the chambers and the chambers fit within the base. This embodiment is advantageous because the separate modular units may be easily moved and cleaned. It is particularly advantageous to have the chamber and the base as separate units so that the chamber may be easily removed from the base. Further, the units may be sized such that each will accommodate the desired amount of fluid. The inside diameter and length of the cylinders may also be sized to interface with different size probes lengths and diameters. It is particularly advantageous to provide components which are sufficiently large enough to accommodate large amounts of fluid. Still further, it is also particularly advantageous to construct the components from materials which will withstand the harsh conditions and materials required during many reactions, such as general chemical synthesis. It is also particularly advantageous to provide the modular components with close tolerances such that they may be combined to form a water tight unit. Such a water tight unit allows for careful control of the waste materials and eliminates the risk of contamination of the surrounding areas.

The wash station of the present invention also provides a method for simultaneously washing multiple probes in a robotic system. In order to wash probes using the wash station of the invention, the probe is first inserted into the hole on the top end of the cylinder. Initially, the cylinder may be contained within the chamber or it may be independent of the chamber. The entire length of the cylinder is inserted into the chamber in a manner such that, as best illustrated in FIGS. 5 and 11, the lower end of the cylinder protrudes from the bottom of the chamber and extends into a pocket in the base. Wash liquid is forced upward from the bottom of the cylinder and over the entire length of the probe within the cylinder. The liquid flows upward and ultimately flows out over the top of the cylinder. The waste liquid is then collected in the drain channel in the base where it flows on to the opening and out of the wash station. This method of cleaning allows for the simultaneous cleaning of both the interior and the exterior of multiple probes. In addition, the wash station of the present invention may be utilized without the cylinder. This embodiment is particularly useful for the function of dispensing excess reagents. To perform this wash function, the probe tip is aligned over or in the drain or drain channel in the base and the excess reagent is then drained.

While there have been described what are presently believed to be the preferred embodiments of the present invention, those skilled in the art will realize that various changes and modifications may be made to the invention without departing from the spirit of the invention, and it is intended to claim all such changes and modifications as fall within the scope of the invention.

We claim:

1. A wash station for simultaneously washing multiple robotic system probes comprising:

a plurality of cylinders, wherein each cylinder has an upper end and a lower end and is provided with an opening throughout the entire length of the cylinder sufficient to accommodate one probe and allow for liquid to flow within the cylinder to wash the probe;

a plurality of chambers, wherein each of the chambers has an upper portion and a lower tip and is provided with an opening throughout the entire length of the chamber sufficient to accommodate at least one of the cylinders; and a base unit which is provided with an opening sufficient to accommodate the plurality of chambers.

2. A wash station according to claim 1, wherein the base further comprises a means for receiving the lower end of the cylinders and an opening for facilitating the drainage of the liquid which has flowed through the cylinders out of the wash station.

3. A wash station according to claim 2, wherein the means for drainage comprises a drain channel in alignment with an opening in the base.

4. A wash station according to claim 3, wherein alignment means are provided for aligning the plurality of chambers within the base.

5. A wash station according to claim 4, wherein the alignment means comprises a dowel.

6. A wash station according to claim 3, wherein the means for receiving the lower ends of the cylinders comprises a plurality of pockets.

7. A wash station according to claim 6, wherein the each of the plurality of pockets is of sufficient size so as to accommodate the lower end of one cylinder in a watertight manner.

8. A wash station according to claim 6, wherein the drain channel is positioned adjacent to the plurality of pockets.

9. A wash station according to claim 6, wherein a plurality of individual drains are provided within the base such that each chamber accommodated within the base has access to a separate individual drain.

10. A wash station according to claim 9 wherein the plurality of individual drains each empty into a central drain channel.

11. A wash station according to claim 1, wherein the plurality of chambers are pressure fitted within the base.

12. A wash station according to claim 1, wherein the upper portion of the chamber has a greater diameter than the lower tip of the chamber.

13. A wash station according to claim 12, wherein a pressure fit is created between the upper portion of the chamber and an opening is created between the lower tip of the cylinder and the chamber.

14. A method for washing probes used in robotic systems using the wash station of claim 1.

15. A method for washing probes used in robotic systems comprising the steps of:

a) providing an apparatus comprising:

a plurality of cylinders, wherein each cylinder has an upper end and a lower end and is provided with an opening throughout the entire length of the cylinder sufficient to accommodate one probe and allow for liquid to flow within the cylinder to wash the probe;

a plurality of chambers, wherein each of the chambers has an upper portion and a lower tip and is provided with an opening throughout the entire length of the chamber sufficient to accommodate at least one of the cylinders; and a base unit which is provided with an opening sufficient to accommodate the plurality of chambers;

b) providing a wash liquid within the plurality of cylinders;

c) immersing a probe within one or more of the plurality of chambers;

d) allowing the wash liquid to flow upward along the probe;

e) draining the wash liquid from the wash station; and f) removing the probe from the wash station.

* * * * *